United States Patent

Shino et al.

Patent Number: 5,292,521
Date of Patent: Mar. 8, 1994

[54] SOLID ORAL PREPARATION CONTAINING A PYRROLIDINE DERIVATIVE WITH A CATECHOL GROUP

[75] Inventors: Mitsumasa Shino, Ibaraki; Sachiyuki Hamano, Kanagawa, both of Japan

[73] Assignee: Eisai Co., Ltd., Tokyo, Japan

[21] Appl. No.: 777,272

[22] PCT Filed: Apr. 5, 1991

[86] PCT No.: PCT/JP91/00453
§ 371 Date: Nov. 26, 1991
§ 102(e) Date: Nov. 26, 1991

[87] PCT Pub. No.: WO91/15204
PCT Pub. Date: Oct. 17, 1991

[30] Foreign Application Priority Data

Apr. 6, 1990 [JP] Japan .................................. 2-91727

[51] Int. Cl.$^5$ .................. A61K 31/395; A61K 31/40
[52] U.S. Cl. .................. 424/484; 514/424; 514/426; 514/429; 424/464; 424/451; 424/489
[58] Field of Search ............. 424/484; 514/424, 426, 514/429

[56] References Cited

U.S. PATENT DOCUMENTS 4,732,892  3/1988  Sarpotdar et al. .................. 514/178

FOREIGN PATENT DOCUMENTS

| 81006 | 6/1983 | European Pat. Off. . |
| 0229652 | 7/1987 | European Pat. Off. . |
| 0264888 | 4/1988 | European Pat. Off. . |
| 286293 | 12/1988 | European Pat. Off. . |
| 0321870 | 6/1989 | European Pat. Off. . |
| 365134 | 11/1989 | European Pat. Off. . |
| 381235 | 8/1990 | European Pat. Off. . |

Primary Examiner—Thurman K. Page
Assistant Examiner—Raj Bawa
Attorney, Agent, or Firm—Flynn, Thiel, Boutell & Tanis

[57] ABSTRACT

An oral solid preparation comprising an organic acid or its salt and a catechol compound. The catechol compound is, for example, a pyrrolidine derivative having a catechol group of the following general formula (I). It exhibits an improved absorbability in vivo.

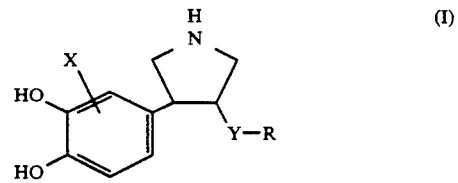

17 Claims, 6 Drawing Sheets

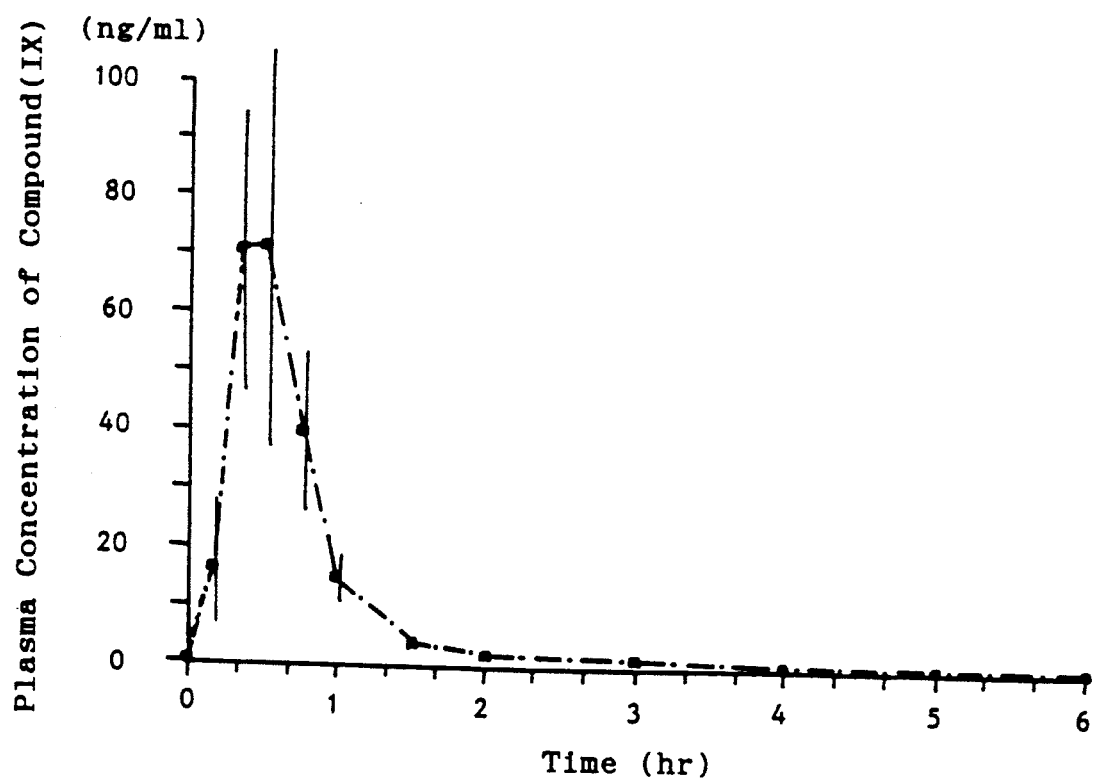
F I G . 4

SOLID ORAL PREPARATION CONTAINING A PYRROLIDINE DERIVATIVE WITH A CATECHOL GROUP

FIELD OF THE INVENTION

The present invention relates to a solid oral preparation containing a catechol compound or a pharmacologically acceptable salt thereof. In particular, the present invention relates to the preparation having an improved absorbability.

PRIOR ART

The term "catechol compound and pharmacologically acceptable salt thereof" as used in the present invention (hereinafter referred to as the compounds of the present invention) include compounds each having a catechol group of the following formula (IV) or a catechol ring of the following formula (V) in the molecule:

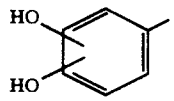

(IV)

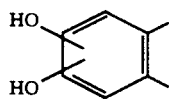

(V)

wherein two OH groups are at the positions ortho to each other.

Examples of the catechol compounds include pyrrolidine derivatives of the following general formula (I) and compounds of the following formulae (II) and (III):

(I)

wherein X represents a hydrogen atom, a halogen atom or a lower alkyl group, Y represents a group of the formula: $-(CH_2)_n-$ in which n is zero or an integer of 1 or 2, a group of the formula:

in which p is zero or an integer of 1 or 2, a group of the formula: $-O-$ or a group of the formula: $-NH-$, and R represents a substituted or unsubstituted phenyl group or a substituted or unsubstituted naphthyl group or a heteroaryl group.

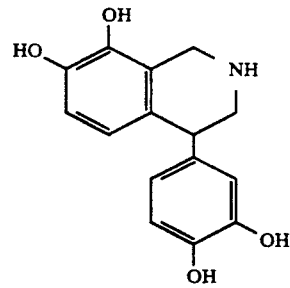

(II)

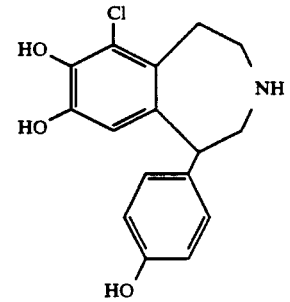

(III)

The compounds of the present invention have a dopamine effect and are expected to be usable as a drug, i.e. a hypotensive having an effect of accelerating the renal blood circulation. A patent application on the compounds of the above general formula (I) and the use thereof as the drug have already been filed (Japanese Patent Laid-Open No. 254349/1989).

When the compound of the present invention is orally administered, the migration thereof into the circulating blood is only slight. For example, the bioavailability thereof used in an amount of around an efficacious amount is only 4 to 5% when it is given to beagles by oral administration as will be shown in the following experimental examples. Although the reasons therefor have not been fully elucidated, it is conceivable that since this compound has a catechol group or a catechol ring in its structure, it is easily subjected to conjugation and is apt to experience the first-pass effect at the absorption site and that in a neutral to alkaline zone, it is chemically unstable and, therefore, it is inclined to be subjected to an oxidative destruction in the intestinal tract as the absorption site.

DISCLOSURE OF THE INVENTION

After intensive investigations made for the purpose of improving the bioavailability of the compounds of the present invention under the above-described circumstances, the inventors have found that surprisingly the object of the invention can be attained by incorporating at least one compound selected from the group consisting of organic acids and salts thereof. The present invention has been completed on the basis of this finding.

Thus the present invention provides a solid oral preparation containing a catechol compound(s), comprising at least one compound selected from the group consisting of organic acids and salts thereof.

A detailed description will now be made on the present invention.

The compounds of the present invention are catechol compounds, i.e. compounds having a catechol group of the following formula (IV) or a catechol ring of the following formula (V) in the molecule:

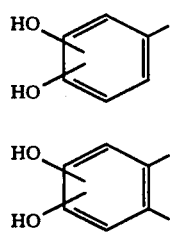

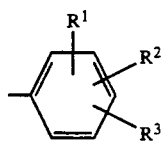

wherein the two OH groups are at the positions ortho to each other.

Examples of these catechol compounds include pyrrolidine derivatives of the above general formula (I) and pharmacologically acceptable salts thereof.

The substituted or unsubstituted phenyl groups represented by R in the general formula (I) are those of the following formula (VI):

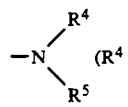

wherein $R^1$, $R^2$ and $R^3$ may be the same or different from one another and each represent a hydrogen atom, a lower alkyl group, a lower alkoxy group, a halogen atom, a hydroxyl group, a trifluoromethyl group or group of the formula:

$$-N \begin{matrix} R^4 \\ R^5 \end{matrix}$$

($R^4$ and $R^5$ being the same or different from each other and each being a hydrogen atom or a lower alkyl group).

The lower alkyl groups in the definition of X in the formula (I) and those of $R^1$, $R^2$, $R^3$, $R^4$ and $R^5$ in the formula (VI) include straight-chain and branched alkyl groups having 1 to 6 carbon atoms, such as methyl, ethyl, n-propyl, n-butyl, isopropyl, isobutyl, 1-methylpropyl, tert-butyl, n-pentyl, 1-ethylpropyl, isoamyl and n-hexyl groups. The most desirable are methyl and ethyl groups.

The halogen atoms in the definition of X in the formula (I) and those of $R^1$, $R^2$ and $R^3$ in the formula (VI) indicate chlorine, iodine, bromine and fluorine.

The lower alkoxy groups in the definition of $R^1$, $R^2$ and $R^3$ indicate those derived from the above-described lower alkyl groups. Examples of the preferred lower alkoxy groups include methoxy groups and ethoxy group.

The substituted naphthyl groups in the definition of R are preferably those substituted with a lower alkyl group typified by methyl group or ethyl group, a lower alkoxy group typified by methoxy group or ethoxy group, a halogen atom, a hydroxyl group or a trifluoromethyl group.

The heteroaryl group in the definition of R indicates a substituted or unsubstituted heterocyclic ring. The heterocyclic ring may contain one or more of nitrogen atom, oxygen atom and sulfur atom. Examples of them include heteroaryl groups containing a nitrogen atom such as imidazolyl groups, e.g. 1-imidazolyl and 2-imidazolyl groups; pyridyl groups, e.g. 3-pyridyl and 4-pyridyl groups; pyrrolyl groups, e.g. 1-pyrrolyl and 3-pyrrolyl groups; pyrazolyl group, indolyl group, indazolyl group, isoquinolyl group, quinolyl group, quinoxalinyl group, quinazolinyl group and imidazopyridyl group, heteroaryl groups containing an oxygen atom in addition to a nitrogen atom, such as oxazolyl group and isoxazolyl group, and heteroaryl groups containing a sulfur atom which are derived from thiophene and benzothiophene. The most desirable heteroaryl groups include pyridyl group, imidazolyl group, thiophenyl group and benzothiophenyl group.

These heteroaryl groups may be substituted with a lower alkyl group such as methyl and ethyl groups; a lower alkoxy group such as methoxy and ethoxy groups; or a halogen atom.

Preferred compounds in those represented by the above general formula (I) in the present invention are those in which R represents a group represented by the formula (VI). They can be represented by the following general formula (VII):

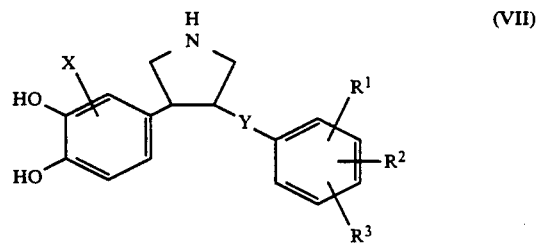

wherein X, Y, $R^1$, $R^2$ and $R^3$ are as defined above.

X in the above general formula (VII) is most desirably a hydrogen atom and $R^1$, $R^2$ and $R^3$ are each preferably a hydroxyl group, a lower alkoxy group or a halogen atom.

Still preferred compounds are those disubstituted with a halogen atom and a hydroxyl group. In these compounds, most desirably, the hydroxyl group is at the m-position and the halogen atom such as a chlorine atom is at the o-position.

Particularly preferred compounds are those wherein R represents a heteroaryl group.

Other examples of the catechol compounds of the present invention include those represented by the following formula (II) or (III):

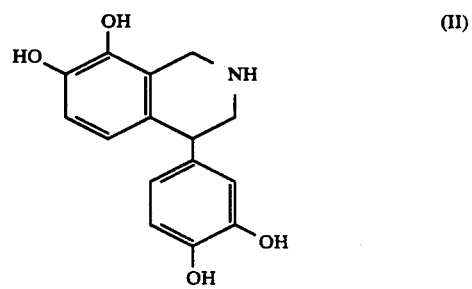

[hereinafter referred to as compound (II)]

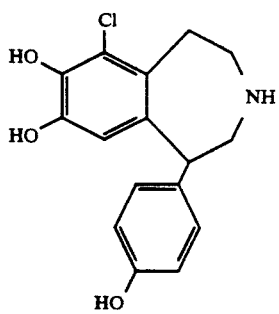

[hereinafter referred to as compound (III)]

The compound (III) is generally called "phenol dopam".

The pharmacologically acceptable salts in the present invention include inorganic acid salts such as hydrochlorides, sulfates, hydrobromides and phosphates; and organic acid salts such as formates, acetates, trifluoroacetates, maleates, fumarates, tartrates, methanesulfonates, benzenesulfonates and toluenesulfonates.

The compounds of the present invention have isomers as will be apparent from their chemical structures. Namely, they have geometrical isomers such as cis- and trans-isomer as well as d and l optically active substances. These isomers are involved in the scope of the present invention as a matter of course.

In the stereoisomers in the present invention, the trans-forms are preferred.

When the compound of the present invention is used as a hypotensive, it is usually given in an amount of 15 to 200 mg/person each time. The dose can be reduced according to the effect in the present invention.

An example of the compounds of the present invention preferably usable as a hypotensive is trans-3-(2-chloro-3-hydroxyphenyl)-4-(3,4-dihydroxyphenyl)pyrrolidine hydrobromide of the following structural formula (VIII):

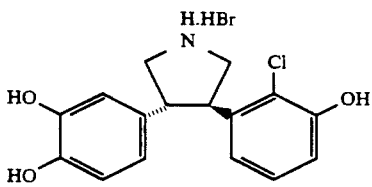

This compound has a melting point of 218° to 219° C. and the following NMR data:

NMR (400 MHz in D$_2$O) δ: 3.45 (1H, t, J=11 Hz), 3.56 (1H, t, J=11 Hz), 3.80~3.89 (1H, m), 4.00 (1H, dd, J=11 Hz, 11 Hz), 4.10 (1H, dd, J=11 Hz, 11 Hz), 4.31 (1H, ddd, J=11 Hz, 11 Hz, 8 Hz), 6.85 (1H, dd, J=8 Hz, 2 Hz), 6.91 (1H, d, J=8 Hz), 6.96 (1H, d, J=2 Hz), 7.04 (1H, dd, J=8 Hz, 2 Hz), 7.18 (1H, d, J=8 Hz), 7.32 (1H, d, J=8 Hz)

This compound will be referred to as "compound (VIII)". The corresponding hydrochloride, instead of the hydrobromide, will be referred to as "compound (IX)".

The organic acids usable in the present invention include ascorbic acid, citric acid, tartaric acid, aspartic acid and cysteine. The amount of one or more compounds selected from the group consisting of the organic acids and salts thereof is not particularly limited and is suitably determined according to the amounts of the compounds of the present invention. It is usually 5 to 80 w/w % based on the preparation of the present invention. It will be apparent from Experimental Examples given below that the bioavailability of the compound (IX) which was 1 when no acid was incorporated thereinto was increased to 7.0, 3.3 and 2.7 by the incorporation of ascorbic acid, citric acid and tartaric acid, respectively. This fact indicated that though the results obtained with ascorbic acid were particularly excellent, they were increased 3.3-fold and 2.7-fold even when citric acid and tartaric acid, respectively, were used.

It will be understood also that the bioavailability of the compound (IX) which was 1 when no additive was incorporated thereinto was increased to about 1.6 and 2.5 by incorporating L-cysteine and L-aspartic acid, respectively. This fact indicated the improvement effect of them.

As for the improvement of the bioavailability of the compounds (II) and (III) by the incorporation of ascorbic acid, it was found that the bioavailability which was 1 when no additive was incorporated thereinto was increased to about 1.4 with the compound (II) and to about 3.3 with the compound (III). It will be understood that the improvement effect on also these compounds were obtained.

The term "bioavailability" herein is defined as follows: a plasma concentration-time curve of a drug after being administered once is prepared in each case of administration by intravenous injection and oral administration with the same amount of the drug, and the availability is represented by the ratio (F) of the area under the plasma concentration-time curve in the case of oral administration ($[AUC]_{PO}$) to the area under the plasma concentration-time curve in the case of intravenous injection ($[AUC]_{IV}$):

$$F = \frac{[AUC]_{PO}}{[AUC]_{IV}}$$

The ratio of an AUC value obtained when one or more compounds selected from the group consisting of organic acids and salts thereof are added to an AUC value obtained when no such compound(s) is (are) added will be referred to as "addition effect ratio".

The solid oral preparation of the present invention may be in any ordinary form of solid oral preparations, such as powder, granule, tablet and capsule, each of which is produced by an ordinary process for producing the same.

BRIEF DESCRIPTION OF THE DRAWINGS

FIG. 4 is a graph showing the plasma concentration-time curve of the compound (IX), which shows the results obtained by adding citric acid.

EXAMPLES

Figure 1:
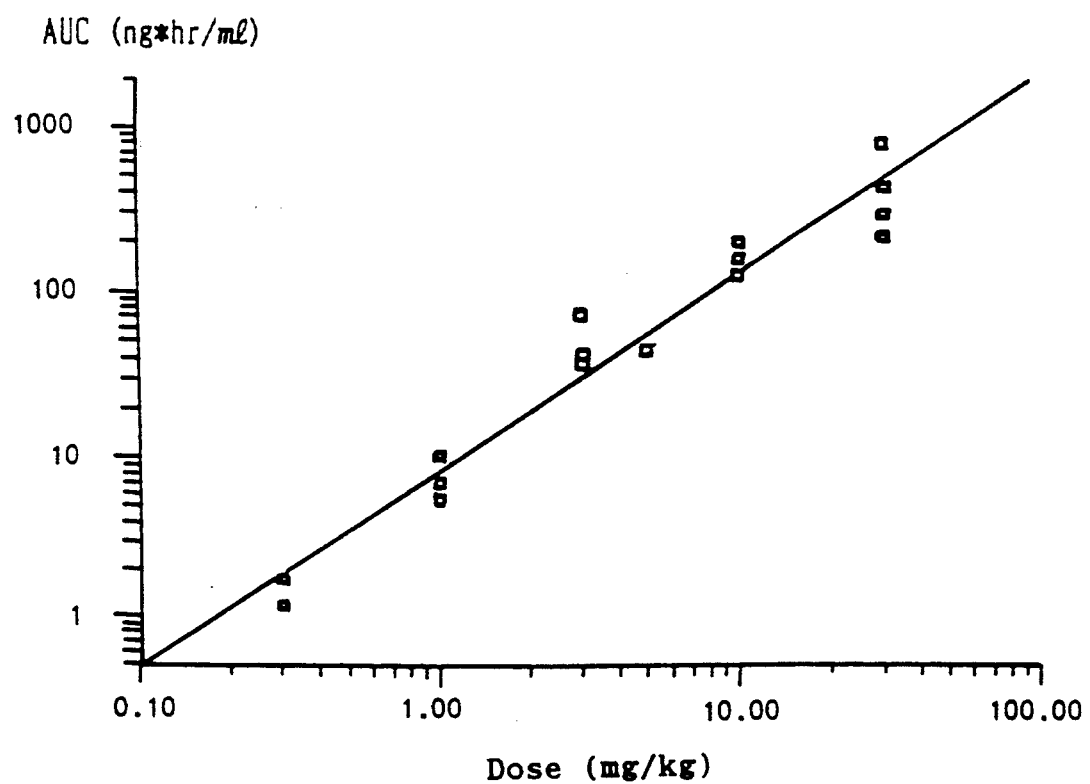
FIG. 1 is a graph showing the correlation between the AUC and the dose.

The following Examples will further illustrate the present invention, which by no means limit the invention.

The following Synthesis Examples will illustrate the processes for synthesizing compounds (II) and (III) used in the following Examples.

SYNTHESIS EXAMPLE 1

Process for Synthesizing Compound (II)

Compound (II) was synthesized by the following synthesis route:

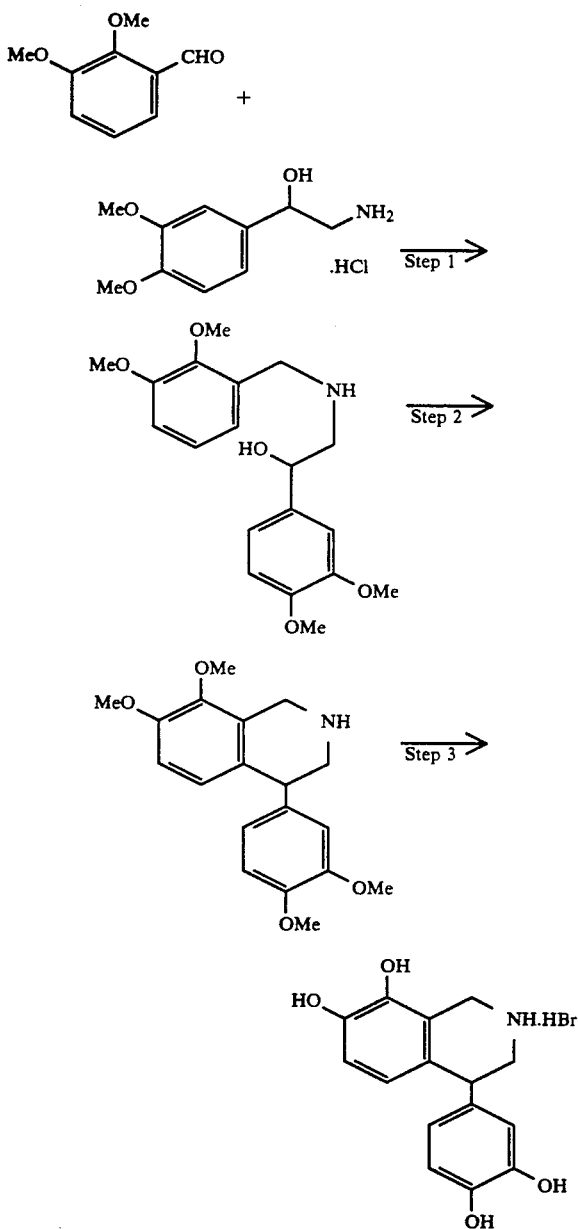

Step 1 Synthesis of α-[[(2,3-dimethoxybenzyl)amino]methyl]-3,4-dimethoxybenzyl alcohol α-Aminomethyl-3,4-dimethoxybenzyl alcohol hydrochloride (5.84 g, 25 mmol) was suspended in methanol (30 ml). 2,3-Dimethoxybenzaldehyde (5 g, 30 mmol) was added to the suspension and then triethylamine (3.83 ml, 27.5 mmol) was added dropwise thereto under stirring at room temperature. The resultant solution was heated under reflux for 30 minutes and then sodium borohydride (1.4 g, 37 mmol) was slowly added thereto under stirring under cooling with ice. After the completion of foaming, the solvent was distilled off under reduced pressure. Water was added to the residue, which was made acidic with 3N hydrochloric acid and washed with ether. The cistern was made basic with aqueous ammonia and then subjected to extraction with dichloromethane. The dichloromethane layer was washed with water and then a saturated sodium chloride aqueous solution and dried over anhydrous magnesium sulfate. The solvent was distilled off under reduced pressure and the resultant crystals were washed with isopropyl ether to obtain 6.56 g of α-[[(2,3-dimethoxybenzyl)amino]methyl]-3,4-dimethoxybenzyl alcohol.

NMR (CDCl$_3$) δ:2.67 (1H, dd), 2.86 (1H, dd) 3.76~3.89 (14H, m), 4.60~4.70 (1H, m) 6.78~7.04 (6H, m)

Step 2 Synthesis of 7,8-dimethoxy-4-(3,4-dimethoxyphenyl)-1,2,3,4-tetrahydroisoquinoline α-[[(2,3-Dimethoxybenzyl)amino]methyl]-3,4-dimethoxybenzyl alcohol 6.56 g, 18.9 mmol) was dissolved in trifluoroacetic acid (50 ml). Concentrated sulfuric acid was added to the solution under stirring and under cooling with ice and the reaction was conducted under these conditions for 40 minutes. The reaction solution was concentrated. Water was added to the residue and then it was made basic with aqueous ammonia under stirring and under cooling with ice. After extraction with dichloromethane, the dichloromethane layer was washed with a saturated sodium chloride aqueous solution and dried over anhydrous magnesium sulfate. The solvent was distilled off under reduced pressure and the resultant crystals were washed with isopropyl ether to obtain 5.23 g of 7,8-dimethoxy-4-(3,4-dimethoxyphenyl)-1,2,3,4-tetrahydroisoquinoline.

mp 104°~105° C.

NMR (CDCl$_3$) δ:3.04 (1H, dd), 3.32 (1H, dd) 3.83 (3H, s), 3.84 (3H, s), 3.87 (3H, s) 3.99 (1H, m), 4.14 (2H, q) 6.58 (1H, d), 6.63 (1H, d), 6.64 (1H, d) 6.71 (1H, d), 6.78 (1H, d)

Step 3 Synthesis of 7,8-dihydroxy-4-(3,4-dihydroxyphenyl)-1,2,3,4-tetrahydroisoquinoline hydrobromide 48% hydrobromic acid (30 ml) was added to 7,8-dimethoxy-4-(3,4-dimethoxyphenyl)-1,2,3,4-tetrahydroisoquinoline (1.5 g, 4.5 mmol) and the mixture was heated under reflux in a nitrogen stream for 3 hours. The reaction solution was cooled and crystals thus formed were separated by filtration and recrystallized from methanol/chloroform to obtain 0.4 g of 7,8-dihydroxy-4-(3,4-dihydroxyphenyl)-1,2,3,4-tetrahydroisoquinone hydrobromide.

| Elementary analysis for C$_{15}$H$_{16}$NO$_4$Br | | | |
|---|---|---|---|
| | C (%) | H (%) | N (%) |
| Calcd. | 50.87 | 4.55 | 3.95 |
| found | 50.48 | 4.45 | 3.57 | mp 230° C. or above

MS (FAB) 274 (M+ +1)

NMR (DMSO-d$_6$) δ:3.17 (1H, m), 3.47 (1H, m) 4.04~4.25 (3H, m) 6.09 (1H, d), 6.46 (1H, dd) 6.49 (1H, d), 6.64 (1H, d), 6.68 (1H, d) 8.80~9.11 (5H, m), 9.39 (1H, s)

SYNTHESIS EXAMPLE 2

Process for Synthesis of Compound (III)

Compound (III) (phenol dopam) was synthesized by the following synthesis route:

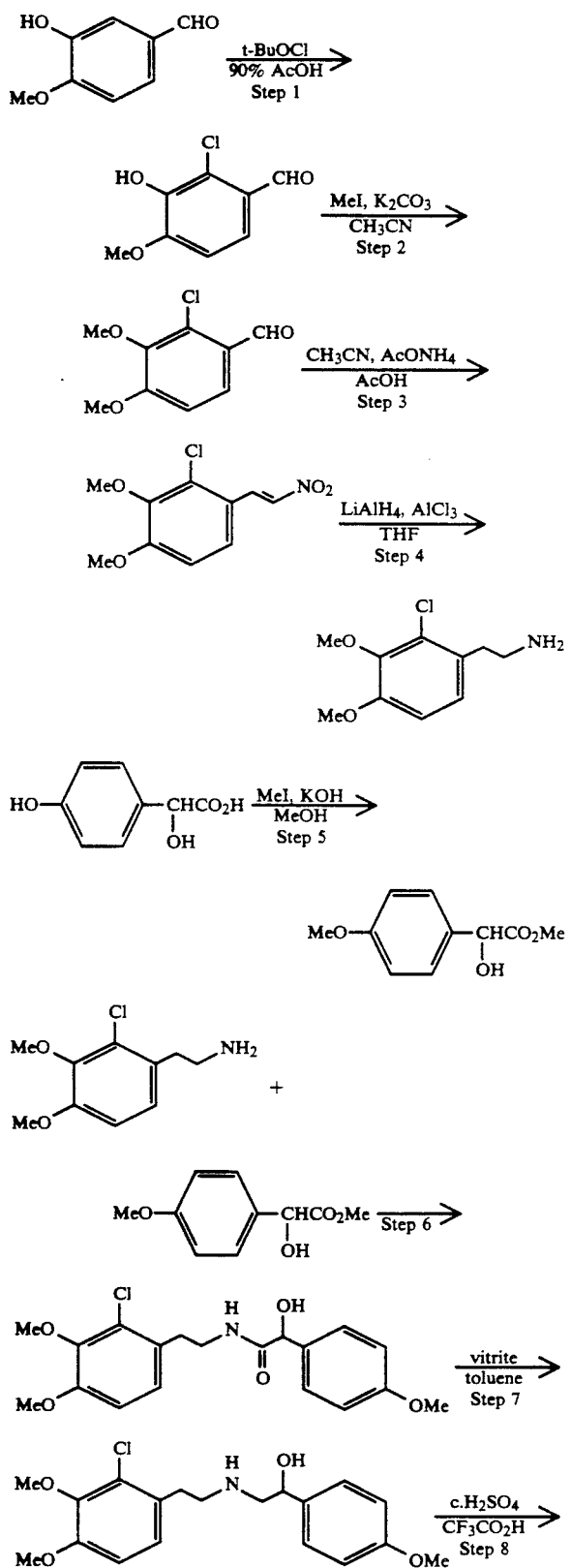

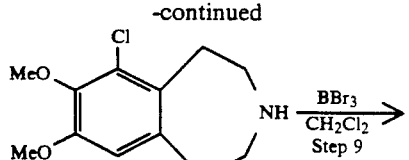

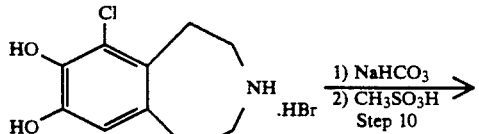

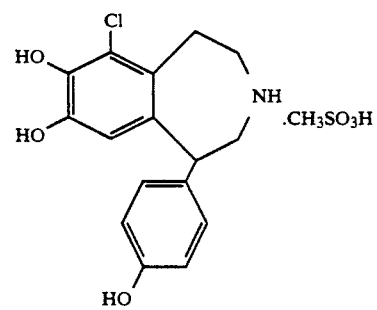

Step 1 Synthesis of 2-chloro-3-hydroxy-4-methoxybenzaldehyde 41.2 g (0.271 mol) of isovanillin was dissolved in 160 ml of 90% AcOH under heating. 29.41 g of t-BuOCl was added dropwise to the solution while it was kept at 35° to 40° C. The solution was stirred at room temperature for 3 hours and then 200 ml of ether was added thereto. The mixture was left to stand overnight and crystals thus formed were separated by filtration and washed with ether. 42.0 g of the crude crystals were recrystallized from acetonitrile to obtain 35 g of 2-chloro-3-hydroxy-4-methoxybenzaldehyde (69%).

mp 203°~205° C.

NMR (90 MHz, DMSO-$d_6$) δ:3.94 (3H, s), 7.10 (1H, d), 7.42 (1H, d), 9.84 (1H, s), 10.16 (1H, s)

Step 2 Synthesis of 2-chloro-3,4-dimethoxybenzaldehyde 184 g (0.986 mol) of 2-chloro-3-hydroxy-4-methoxybenzaldehyde was dissolved in 2 l of $CH_3CN$. 204 g (1.476 mol) of $K_2CO_3$ and 298 g (2.096 mol) of $CH_3I$ were added to the solution, which was heated under reflux for 4 hours.

After cooling, the crystals were separated by filtration and the mother liquor was concentrated under reduced pressure. 800 ml of water and 600 ml of $CHCl_3$ were added to the residue to conduct extraction. The $CHCl_3$ layer was washed with 500 ml of 10% NaOH and a saturated NaCl aqueous solution. It was dehydrated over $MgSO_4$ and concentrated to dryness under reduced pressure to obtain 189.49 g (96%) of 2-chloro-3,4-dimethoxybenzaldehyde.

mp 70°~72° C.

NMR (90 MHz, CDCl$_3$) δ:3.88 (3H, s), 3.96 (3H, s), 6.92 (1H, d), 7.72 (1H, d), 10.28 (1H, s)

Step 3 Synthesis of 2-chloro-3,4-dimethoxy-β-nitrostyrene 189 g of 2-chloro-3,4-dimethoxybenzaldehyde was dissolved in 517 ml of AcOH by heating. 64 g of AcONH$_4$ and 169 ml of CH$_3$CN were added to the solution at 60° C. and the reaction was conducted at 100° C. for 2 hours. After the completion of the reaction, 350 ml of water was added to the reaction mixture to cool it and the mixture was left to stand overnight. Crystals thus formed were separated by filtration and recrystallized from 600 ml of MeOH to obtain 139.73 g (yield: 60.9%) of 2-chloro-3,4-dimethoxy-β-nitrostyrene.

mp 86°~90° C.

NMR (90 MHz, CDCl$_3$) δ: 3.88 (3H, s), 3.95 (3H, s), 6.90 (1H, d), 7.38 (1H, d), 7.56 (1H, d), 8.36 (1H, d)

Step 4 Synthesis of 2-(2-chloro-3,4-dimethoxyphenyl)ethylamine 28.8 g of LiAlH$_4$ was dispersed in 920 ml of THF in a nitrogen stream. A solution of 100 g of AlCl$_3$ in 1220 ml of THF was added dropwise to the dispersion under cooling at 0° C. After the completion of the addition, the mixture was stirred for 1 hour and a solution of 92 g of 2-chloro-3,4-dimethoxy-β-nitrostyrene obtained in Step 3 in 1440 ml of THF was added dropwise thereto. After the mixture was stirred at room temperature overnight, 122 ml of water was carefully added dropwise thereto under cooling with ice and then 122 ml of concentrated NH$_4$OH was added dropwise thereto. The mixture was stirred for 1 hour and crystals thus precipitated were separated by filtration and the mother liquor was concentrated under reduced pressure. 300 ml of ethyl acetate and a 10% NaOH aqueous solution were added to the residue to conduct extraction. After washing with water followed by dehydration over MgSO$_4$ and concentration to dryness under reduced pressure, 2-(2-chloro-3,4-dimethoxyphenyl)ethylamine (63.9 g, 79%) was obtained.

NMR (90 MHz, CDCl$_3$) δ: 1.42 (2H, br), 2.85 (2H, d), 2.93 (2H, d), 3.86 (3H, s), 3.87 (3H, s), 6.76 (1H, d), 6.94 (1H, d)

Step 5 Synthesis of methyl 4-methoxymandelate 50 g of 4-hydroxymandelic acid was dissolved in 500 ml of MeOH. 39.9 g of KOH and 101.2 g of CH$_3$I were added to the solution and the reaction was conducted at 55° to 62° C. for 16 hours. The reaction solution was concentrated under reduced pressure and MeOH was removed. 800 ml of water and 700 ml of CHCl$_3$ were added thereto to conduct extraction. The CHCl$_3$ layer was washed with water and then with a saturated NaCl aqueous solution, dehydrated over MgSO$_4$ and concentrated under reduced pressure. The residue was distilled under reduced pressure to obtain 35.14 g of methyl 4-methoxymandelate.

b.p 120°-140° C./1~2 mmHg

NMR (90 MHz, CDCl$_3$) δ: 3.48 (1H, br), 3.75 (3H, s), 3.79 (3H, s), 5.10 (1H, br), 6.87 (2H, d), 7.30 (2H, d)

Step 6 Synthesis of N-(2-chloro-3,4-dimethoxyphenylethyl)-4-methoxymandelamide 16.86 g of (2-chloro-3,4-dimethoxyphenyl)ethylamine obtained in step 4 was reacted with 15.33 g of methyl 4-methoxymandelate obtained in step 5 at 130° to 140° C. in a nitrogen gas atmosphere for 1.5 hour. After cooling, the reaction mixture was dissolved in 30 ml of ethyl acetate and purified by silica gel chromatography. After development with ethyl acetate/n-hexane (1/1) and then with ethyl acetate, 20.6 g (69%) of N-(2-chloro-3,4-dimethoxyphenylethyl)-4-methoxymandelamide was obtained.

mp 68°~70° C.

NMR (90 MHz, CDCl$_3$) δ: 2.81 (2H, t), 3.44 (2H, q), 3.75 (3H, s), 3.82 (6H, s), 4.22 (1H, d), 4.86 (1H, d), 6.50 (1H, br), 6.57~6.70 (2H, m), 6.80 (2H, d), 7.20 (2H, d)

Step 7 Synthesis of N-[2-hydroxy-2-(4-methoxyphenyl)ethyl]-2-(2-chloro-3,4-dimethoxyphenyl)ethylamine 10.58 g of N-(2-chloro-3,4-dimethoxyphenylethyl)-4-methoxymandelamide was dissolved in 105.8 ml of toluene. A solution of 16.5 ml of Vitrite in 16.5 ml of toluene was added dropwise to the solution at room temperature. Then the reaction was conducted at 50° C. for 4 hours. After cooling, 100 ml of a 10% NaOH solution was added dropwise thereto and the mixture was left to stand overnight. Crystals thus formed were separated by filtration, washed with water and dried to obtain 7.87 g (yield: 77.2%) of N-[2-hydroxy-2-(4-methoxyphenyl)ethyl]-2-(2-chloro-3,4-dimethoxyphenyl)ethylamine.

mp 117°~120° C.

NMR (90 MHz, CDCl$_3$) δ: 2.35 (3H, br), 2.70~2.90 (5H, m), 3.80 (3H, s), 3.85 (6H, s), 4.64 (1H, dd), 6.64~6.98 (3H, m), 7.10~7.36 (3H, m)

Step 8 Synthesis of 6-chloro-2,3,4,5-tetrahydro-7,8-dimethoxy-1-(4-methoxyphenyl)-1H-3-benzazepine 7.87 g of N-[2-hydroxy-2-(4-methoxyphenyl)ethyl]-2-(2-chloro-3,4-dimethoxyphenyl)ethylamine was dissolved in 59 ml of CF$_3$COOH. 1.7 ml of concentrated H$_2$SO$_4$ was added to the solution and the reaction was conducted for 4 hours. After the completion of the reaction followed by concentration under reduced pressure, 100 ml of CHCl$_3$ and 50 ml of 10% NaOH were added to the residue to conduct extraction. The extract was washed with water, dehydrated over MgSO$_4$ and concentrated to dryness under reduced pressure to obtain 6.25 g (yield: 83.5%) of 6-chloro-2,3,4,5-tetrahydro-7,8-dimethoxy-1-(4-methoxyphenyl)-1H-3-benzazepine.

mp 139°~142° C.

NMR (90 Mz, CDCl$_3$) δ: 2.00 (1H, br), 2.80~3.24 (4H, m), 3.30~3.50 (2H, m), 3.66 (3H, s), 3.78 (3H, s), 3.82 (3H, s), 4.18 (1H, dd), 6.33 (1H, s), 6.82 (2H, d), 7.00 (2H, d)

Step 9 Synthesis of 6-chloro-2,3,4,5-tetrahydro-1-(4-hydroxyphenyl)-1H-3-benzazepine-7,8-diol hydrobromide 6.10 g of 6-chloro-2,3,4,5-tetrahydro-7,8-dimethoxy-1-(4-methoxyphenyl)-1H-3-benzazepine obtained in step 8 was dissolved in 176 ml of CH$_2$Cl$_2$. 88.3 ml of a solution of 2M BBr$_3$ in CH$_2$Cl$_2$ was added dropwise thereto at −25° C. for 20 minutes. After the completion of the addition, the reaction mixture was stirred at room temperature for 3 hours and then cooled to −20° C. and 50 ml of MeOH was added dropwise thereto.

The reaction liquid was concentrated under reduced pressure and CH$_2$Cl$_2$ was removed. 20 ml of ethyl acetate was added to the residue in a slurry form. The mixture was cooled and crystals thus formed were separated by filtration, washed with ethyl acetate, and dried to obtain 6.01 g (yield: 88.6%) of 6-chloro-2,3,4,5-tetrahydro-1-(4-hydroxyphenyl)-1H-3-benzazepine-7,8-diol hydrobromide.

mp 275° C. (dec.)

NMR (90 MHz, DMSO) δ: 2.64~3.60 (6H, m), 4.32~4.56 (1H, m), 6.04 (1H, s), 6.76 (2H, d), 6.97 (2H, d), 8.90 (3H, br), 9.40 (2H, br)

Step 10 Synthesis of 6-chloro-2,3,4,5-tetrahydro-1-(4-hydroxyphenyl)-1H-3-benzazepine-7,8-diol methanesulfonate 5.8 g of the hydrobromide obtained in step 9 was dissolved in 90 ml of MeOH. A 5% NaHCO$_3$ aqueous solution was added to the MeOH solution and the mixture was stirred for 10 minutes. Crystals thus formed were separated by filtration and washed with 250 ml of water. The crystals were suspended in 90 ml of MeOH. 1.17 ml of methanesulfonic acid was added thereto and the liquid reaction mixture was dried under reduced pressure to obtain 5.08 g of a crude product.

It was recrystallized from MeOH (200 ml) to obtain 3.6 g (61%) of 6-chloro-2,3,4,5-tetrahydro-1-(4-hydroxyphenyl)-1H-3-benzazepine-7,8-diol methanesulfonate.

mp 270° C. (dec.)

NMR (400 MHz, DMSO) δ: 2.32 (3H, s), 2.90 (1H, dd), 3.15~3.22 (1H, m), 3.33~3.45 (4H, m), 4.44 (1H, dd), 6.09 (1H, s), 6.81 (2H, d), 7.00 (2H, d), 8.79 (1H, br), 8.93 (1H, br), 8.99 (1H, s), 9.46 (1H, s), 9.47 (1H, s)

| Elementary analysis for $C_{17}H_{20}ClNO_6S$ | | | |
|---|---|---|---|
| | C (%) | H (%) | N (%) |
| Calcd. | 50.81 | 5.02 | 3.49 |
| found | 50.95 | 5.04 | 3.32 |

•MS (FAB) 306 (M+1)

EXAMPLE 1

9 g of compound (IX) was thoroughly mixed with 20 g of ascorbic acid and 7 g of lactose in a mortar. 360 mg of the mixture was filled in each of No. 2 gelatin capsules to obtain the oral preparation of the present invention.

| Amounts of components per capsule | |
|---|---|
| compound (IX) | 90 mg |
| ascorbic acid | 200 mg |
| lactose | 70 mg |
| in total | 360 mg |

(filled in No. 2 gelatin capsule)

EXAMPLE 2

6 g of compound (IX) was thoroughly mixed with 20 g of sodium citrate, 20 g of ascorbic acid and 6 g of D-mannitol in a mortar. 520 mg of the mixture was filled in each of No. 1 gelatin capsules to obtain the oral preparation.

| Amounts of components per capsule | |
|---|---|
| compound (IX) | 60 mg |
| sodium citrate | 200 mg |
| ascorbic acid | 200 mg |
| D-mannitol | 60 mg |
| in total | 520 mg |

(filled in No. 1 gelatin capsule)

EXAMPLE 3

3 g of compound (IX) was thoroughly mixed with 15 g of tartaric acid and 9 g of D-mannitol in a mortar. 270 mg of the mixture was filled in each of No. 3 gelatin capsules to obtain the oral preparation.

| Amounts of components per capsule | |
|---|---|
| compound (IX) | 30 mg |
| tartaric acid | 150 mg |
| D-mannitol | 90 mg |
| in total | 270 mg |

(filled in No. 3 gelatin capsule)

EXAMPLE 4

9 g of compound (II) was thoroughly mixed with 20 g of ascorbic acid and 7 g of lactose in a mortar. 360 mg of the mixture was filled in each of No. 2 gelatin capsules to obtain the oral preparation of the present invention.

| Amounts of components per capsule | |
|---|---|
| compound (II) | 90 mg |
| ascorbic acid | 200 mg |
| lactose | 70 mg |
| in total | 360 mg |

(filled in No. 2 gelatin capsule)

EXAMPLE 5

9 g of compound (III) was thoroughly mixed with 20 g of ascorbic acid and 7 g of lactose in a mortar. 360 mg of the mixture was filled in each of No. 2 gelatin capsules to obtain the oral preparation of the present invention.

| Amounts of components per capsule | |
|---|---|
| compound (III) | 90 mg |
| ascorbic acid | 200 mg |
| lactose | 70 mg |
| in total | 360 mg |

(filled in No. 2 gelatin capsule)

EXAMPLE 6

3 g of compound (IX) was thoroughly mixed with 15 g of L-aspartic acid and 9 g of D-mannitol in a mortar. 270 mg of the mixture was filled in each of No. 3 gelatin capsules to obtain the oral preparation.

| Amounts of components per capsule | |
|---|---|
| compound (IX) | 30 mg |
| L-aspartic acid | 150 mg |
| D-mannitol | 90 mg |
| in total | 270 mg |

(filled in No. 3 gelatin capsule)

EXAMPLE 7

3 g of compound (IX) was thoroughly mixed with 15 g of L-cysteine and 9 g of D-mannitol in a mortar. 270 mg of the mixture was filled in each of No. 3 gelatin capsules to obtain the oral preparation.

| Amounts of components per capsule | |
|---|---|
| compound (IX) | 30 mg |
| L-cysteine | 150 mg |
| D-mannitol | 90 mg |

-continued

| Amounts of components per capsule | |
|---|---|
| in total | 270 mg |

(filled in No. 3 gelatin capsule)

EXAMPLE 8

9 g of trans-3-benzyl-4-(3,4-dihydroxyphenyl)pyrrolidine hydrobromide [compound (X)] was thoroughly mixed with 20 g of ascorbic acid and 7 g of lactose in a mortar. 360 mg of the mixture was filled in each of No. 2 gelatin capsules to obtain the oral preparation of the present invention.

| Amounts of components per capsule | |
|---|---|
| compound (X) | 90 mg |
| ascorbic acid | 200 mg |
| lactose | 70 mg |
| in total | 360 mg |

(filled in No. 2 gelatin capsule)

EFFECT OF THE INVENTION

The following Experimental Examples will further illustrate the effect of the present invention.

EXPERIMENTAL EXAMPLE 1

1 mg/kg of compound (VIII) was administered to beagles by intravenous injection and the plasma concentration-time curve thereof of prepared to find that the half-life composed of three phases (phases a, b and c). The drug disposition parameters were as given in Table 1.

TABLE 1

| | $C_p^0$ ng/ml | $V_c$ l/kg | $CL_{total}$ ml/min/kg | $t_{\frac{1}{2}a}$ min | $t_{\frac{1}{2}b}$ min | $t_{\frac{1}{2}c}$ min | MRT min |
|---|---|---|---|---|---|---|---|
| 1 mg/kg iv | 2286 | 0.44 | 78.0 | 1.3 | 8.11 | 26.9 | 14.5 |

MRT in Table 1 indicates the mean residence time in the plasma.

EXPERIMENTAL EXAMPLE 2

Compound (VIII) or compound V was formulated into a powder of ten-fold dilution with lactose. It was given to beagles in an amount ranging from 0.3 to 30 mg/kg as a capsule by oral administration and the plasma concentration-time curve thereof was prepared. From the curve, the correlation between the AUC and the dose as shown in FIG. 1 was obtained. The regression line equation was as follows:

log'(AUC) = 1.218 log(dose) + 0.894

Since the gradient is 1.218, the AUC value is increased 16.5-fold with the dose is increased 10-fold. The bioavailability calculated from the regression line equation is shown in Table 2.

TABLE 2

| Dose (mg/kg PO) | 10 | 5 | 3 | 1 |
|---|---|---|---|---|
| AUC (ng*hr/ml) | 129 | 54.9 | 29.9 | 7.83 |
| Bioavailability (%) | 6.0 | 5.1 | 4.7 | 3.7 |

It will be apparent that the bioavailability is 4 to 5% when the efficacious oral dose is around 3 to 5 mg/kg.

EXPERIMENTAL EXAMPLE 3

Samples

Compound (IX) and ascorbic acid, citric acid or tartaric acid were weighed, pulverized thoroughly and mixed together in an agate mortar. The mixture was divided into portions and filled in gelatin capsules (No. 1 or No. 00) and the gap in each capsule was further filled with lactose to obtain a sample. Separately, compound (IX) was formulated into a powder of five-fold dilution with lactose and filled in capsules in a similar manner to that described above to obtain a control sample.

The dose of compound (IX) was adjusted to 3 mg/kg in all the cases, while that of ascorbic acid was adjusted to three levels, i.e. 3 mg/kg, 9 mg/kg and 15 mg/kg and that of each of citric acid and tartaric acid was adjusted to one level of 15 mg/kg.

Method (a) Administration and collection of blood sample

The capsule of compound (IX) was given to each of 4 beagles (average body weight 9.53 kg) together with 30 ml of water by oral administration after fasting overnight (14 hours). The experiment was conducted by the crossover administration method while the beagles were kept fasting. 3 ml of the whole blood was sampled through a vein of a foreleg by means of a heparinized syringe, cooled with ice/water and centrifuged (1200 rpm, 3 min, 4° C.). The blood plasma was separated and a citrate buffer solution (pH 3.5, 50 μl) was added thereto to adjust the pH to 5.0. The plasma thus treated was kept frozen at −20° C. The points of collection of blood samples were before the administration and 10, 20, 30 and 45 minutes and 1, 1.5, 2, 3, 4, 5 and 6 hours after the administration. (b) Method of analysis of concentration of unchanged substance in blood plasma An internal standard substance (IS 50 ng in 50 μl) was added to 1 ml of blood plasma. After extraction with 5 ml of ethyl acetate, the solvent was distilled off. 100 μl of a citrate buffer solution (pH 3.5) was added thereto to form a solution again, which was washed with 1 ml of diethyl ether. The lower layer was separated and 50 μl of methanol was added thereto. 50 to 100 μl thereof was injected into an instrument for high-performance liquid chromatography (HPLC) for determination. Separately, blood plasma containing known amounts of compound (IX) and IS was treated to prepare an addition/recovery calibration curve. The concentration was determined from the ratio of the peak height of compound (IX) to that of IS. The detection limit in this method was 0.2 ng/ml of plasma.

(c) HPLC determination conditions

A HPLC pump used was CCPD mfd. by Toyo Soda Mfg. Co., Ltd. 1.5 ml/min of a citrate buffer (pH 3.5)/methanol mixture 80:1 (V/V) was introduced therein. The sample was injected into the instrument with a WISP 710B auto-sampler mfd. by Waters at intervals of about 50 minutes. A reversed phase Nucleosil (trade name) 7C6H5 column (4.6×250 mm) with a prefilter was used as the analysis column. The detector used was an ECD-100 electrochemical detector mfd. by Acome. The voltage was +650 mV (against a SEC electrode).

The citrate buffer solution (pH 3.5) was prepared by dissolving 26.25 g of citric acid, 16.58 g of anhydrous sodium acetate, 12.25 g of sodium hydroxide, 0.8375 g of disodium ethylenediaminetetraacetate, 93.8 ml of glacial acetic acid and 35.9 ml of 60% perchloric acid in 2500 ml of distilled water.

Results

Figure 2:
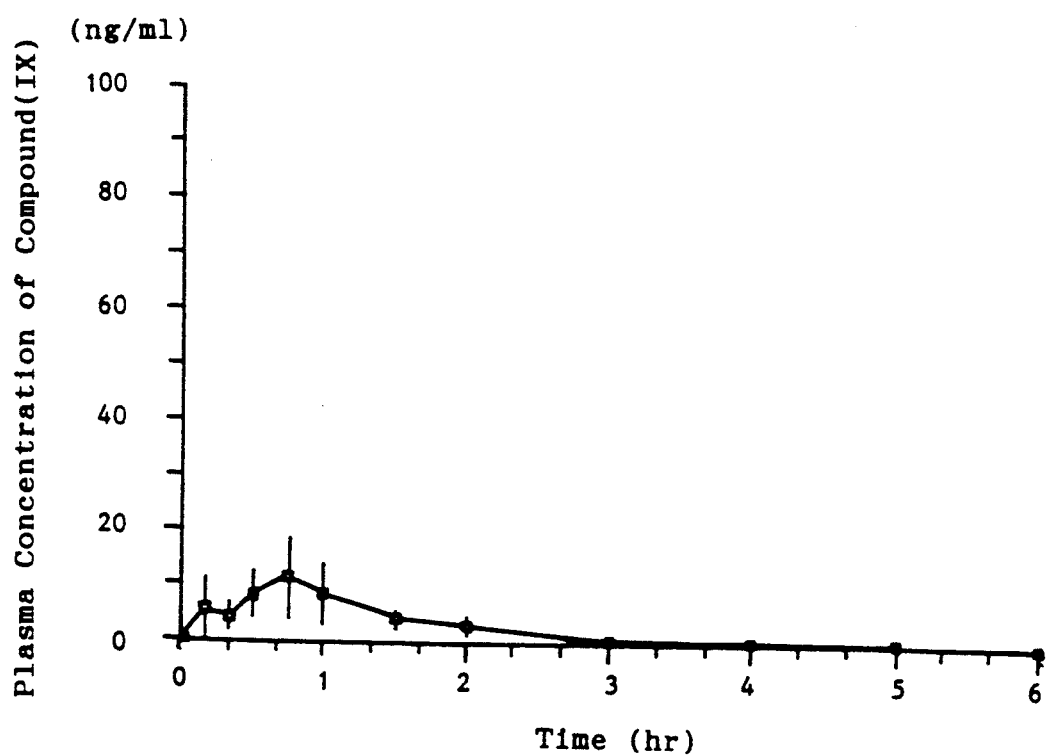
FIG. 2 is a graph showing the plasma concentration-time curve of the compound (IX), which shows the results of a control sample.
Figure 3:
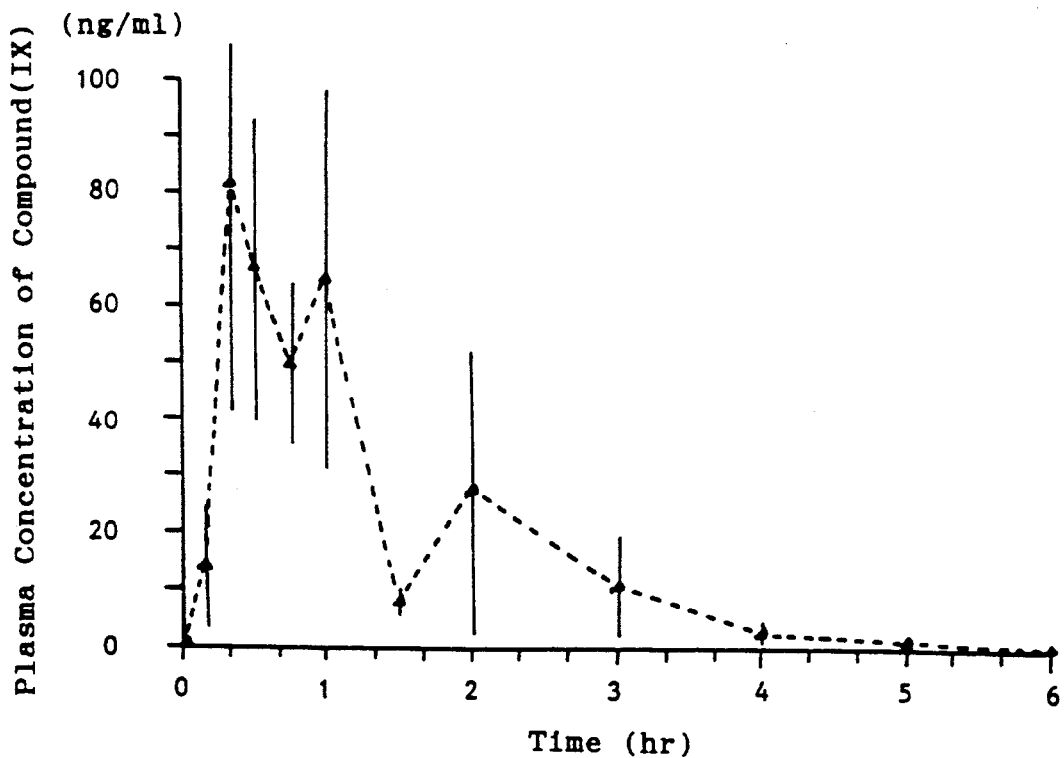
FIG. 3 is a graph showing the plasma concentration-time curve of the compound (IX), which shows the results obtained by adding ascorbic acid.
Figure 5:
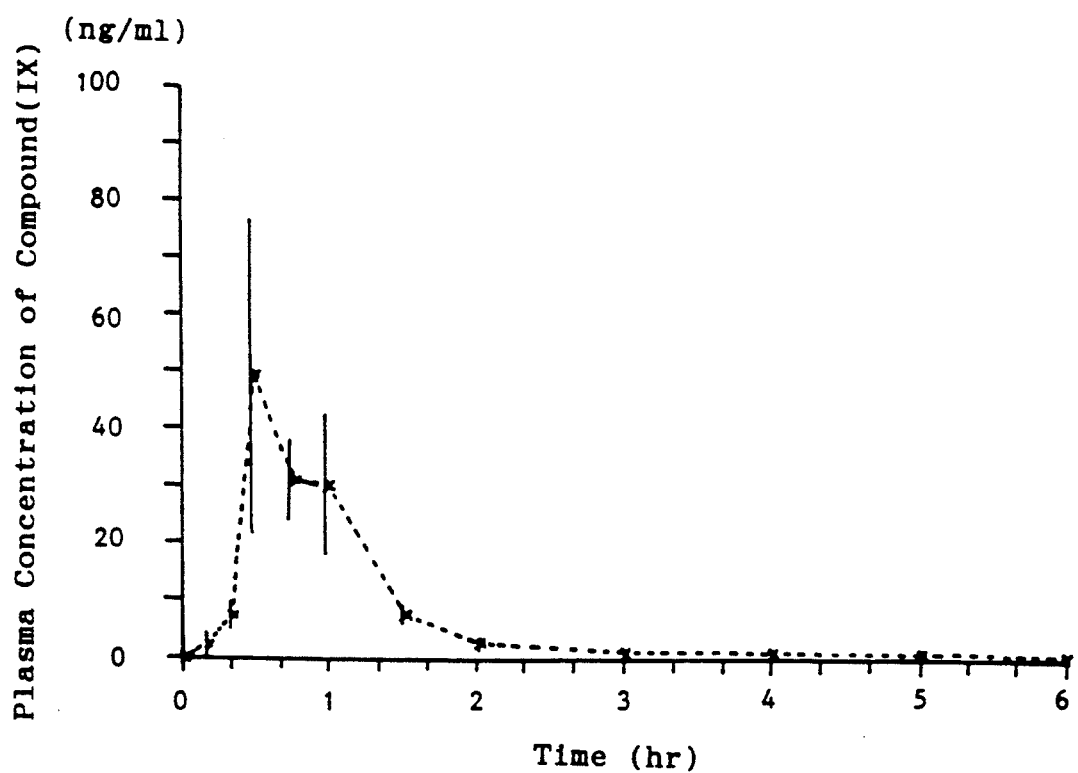
FIG. 5 is a graph showing the plasma concentration-time curve of the compound (IX), which shows the results obtained by adding tartaric acid.

The results are given in FIGS. 2 through 5. FIG. 2 indicates the plasma concentration-time curve when the control sample was used, FIG. 3 indicates a similar curve when 15 mg/kg of ascorbic acid was used as the test sample, FIG. 4 indicates a similar curve when 15 mg/kg of citric acid was used as the test sample, and FIG. 5 indicates a similar curve when 15 mg/kg of tartaric acid was used as the test sample.

Figure 6:
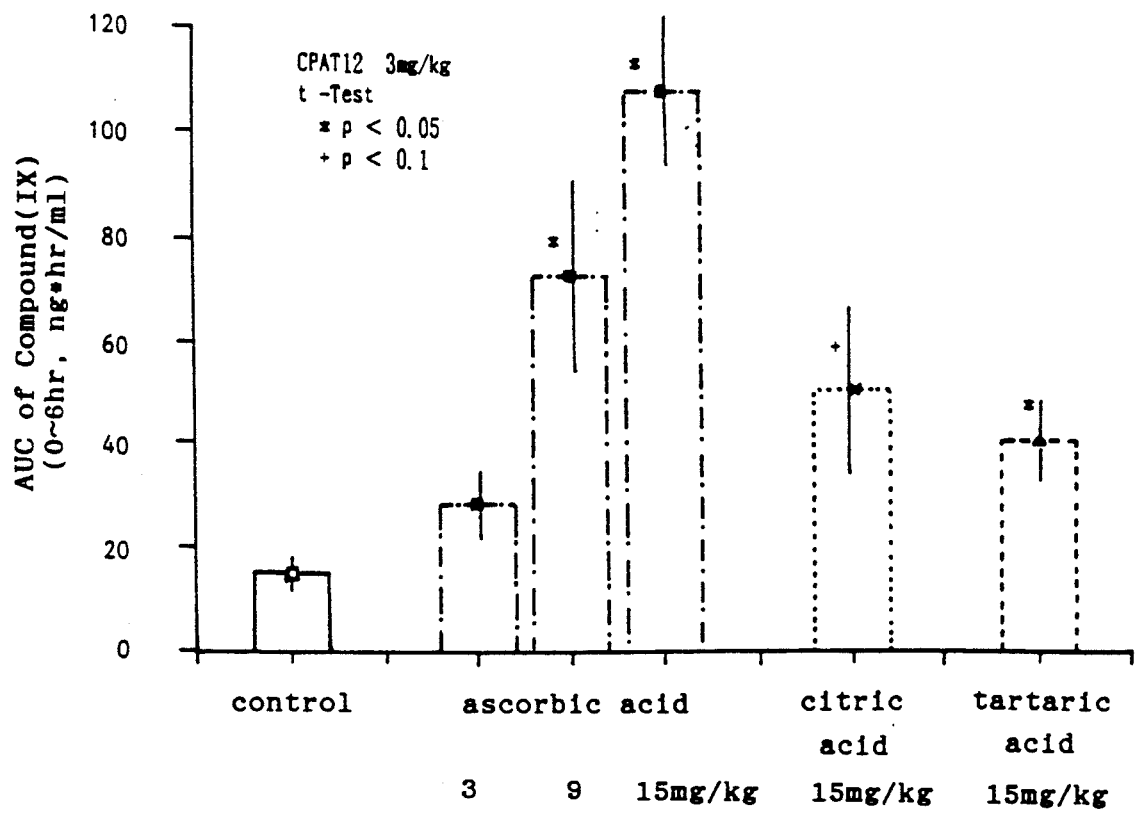
FIG. 6 is a bar graph showing the AUC values of the samples as compared with one another.

The AUC value in the period of 0 to 6 hours was determined from each of these curves. The results are given in FIG. 6, which is a bar graph for the comparison of the AUC values of the respective samples.

The drug disposition parameters of each sample were determined from the obtained data. The results are given in Table 3.

TABLE 3

| Dose of compound (IX) mg/kg | Dose of added organic acid (ratio) mg/kg | n | $T_{max}$ mean ± SE min | $C_{max}$ mean ± SE ng/ml | AUC (0–6 hr) mean ± SE ng*hr/ml | Addition effect ratio |
|---|---|---|---|---|---|---|
| 3 | Ascorbic acid (vitamin C) | | | | | |
| | 3 (1:1) | 4 | 34 ± 4 | 33.8 ± 13.2 | 28.4 ± 6.5 | 1.9 |
| | 9 (1:3) | 4 | 43 ± 26 | 186.7 ± 91.7 | 72.6 ± 18.5 | 4.8 |
| | 15 (1:5) | 4 | 55 ± 24 | 139.1 ± 20.9 | 107.0 ± 14.6 | 7.0 |
| 3 | citric acid | | | | | |
| | 15 (1:5) | 4 | 29 ± 6 | 87.4 ± 30.2 | 50.7 ± 16.5 | 3.3 |
| 3 | Tartaric acid | | | | | |
| | 15 (1:5) | 4 | 45 ± 9 | 61.5 ± 26.3 | 40.4 ± 7.8 | 2.7 |
| 3 | none | 4 | 44 ± 17 | 21.0 ± 5.3 | 15.2 ± 2.8 | 1.0 base |

Notes)
n: number of beagles,
$T_{max}$: time taken for attaining the maximum plasma concentration,
$C_{max}$: maximum plasma concentration,
AUC: area under the plasma concentration-time curve.

It was found from Table 3 that when ascorbic acid, citric acid or tartaric acid was added, the effect of increasing the maximum plasma concentration ($C_{max}$) and the area under the plasma concentration-time curve (AUC) was remarkably improved and that the effect of the addition of ascorbic acid was the best and increased the AUC value 7-fold as compared with the case where no ascorbic acid was added (compound (IX) 3 mg/kg, ascorbic acid 15 mg/kg). When citric acid or tartaric acid was added, the AUC value was increased 3.3-fold and 2.7-fold, respectively, as compared with the case where none of them was added.

EXPERIMENTAL EXAMPLE 4

Samples 350 mg of L-cysteine and 70 mg of lactose were added to 70 mg of compound (IX) and the mixture was thoroughly pulverized and mixed in a mortar. The mixture was filled in each of No. 2 gelatin capsules in such an amount that the dose of compound (IX) would be 3 mg/kg to obtain a preparation.

A similar mixture to that described above was prepared except that L-cysteine was replaced by 350 mg of L-aspartic acid. The mixture was filled in each of No. 2 gelatin capsules in such an amount that the dose of compound (IX) would be 3 mg/kg to obtain a preparation.

A control preparation containing no amino acid comprised a powder of 5-fold dilution of compound (IX) with lactose, and filled in capsules in such an amount that the dose of compound (IX) would be 3 mg/kg.

Method (a) Administration and collection of blood sample

Four beagles were divided into two groups after fasting overnight (14 hours) and a preparation comprising 3 mg/kg of compound (IX) and 15 mg/kg of L-cysteine or L-aspartic acid or a control preparation comprising no amino acid was given together with 30 ml of water by oral administration. No food was given also in the course of collection of blood sample. 3 ml of the whole blood was sampled through a vein of a foreleg by means of a heparinized syringe, cooled with ice/water and centrifuged (1200 rpm, 3 min, 4° C.). The blood plasma was separated and a citrate buffer solution (pH 3.5, 100 μl) was added thereto to adjust the pH to 5.0. The plasma thus treated was kept frozen at −20° C. The points of collection of blood samples were before the administration and 10, 20, 30 and 45 minutes and 1, 1.5, 2, 3, 4, 6 and 8 hours after the administration.

(b) Method of analysis of concentration of unchanged substance in blood plasma

An internal standard substance (IS 20 ng in 200 μl) was added to 1 ml of blood plasma. After dilution with 2 ml of water, the aqueous solution was passed through a BONDELUTE (trade name) C18 column previously washed with 3 ml of methanol containing 0.1% of acetic acid and 9 ml of water. After further washing with 9 ml of water and 2 ml of acetonitrile, the sample was eluted with 1.2 ml of methanol containing 0.1% of perchloric acid. The solvent was distilled off and the residue was dissolved in 200 μl of a 0.1% acetic acid aqueous solution/methanol mixture (2/1, V/V). 50 to 100 μl thereof was injected into an instrument for HPLC for determination. Separately, blood plasma containing known amounts of compound (IX) and IS was treated to prepare an addition/recovery calibration curve. The concentration was determined from the ratio of the peak height of compound (IX) to that of IS. The detection limit in this method was 0.05 ng/ml of plasma.

(c) HPLC determination conditions

A HPLC pump used was CCPD mfd. by Toyo Soda Mfg. Co., Ltd. 1.35 ml/min of an aqueous solution containing 0.1% of perchloric acid and 0.01% of a disodium ethylenediaminetetraacetate/methanol mixture 80:9 (V/V) was introduced therein. The sample was injected into the instrument with a WISP 710B auto-sampler mfd. by Waters at intervals of about 50 minutes. A reversed phase ODS-120 T column (4.6×250 mm) with a prefilter was used as the analysis column. The detector used was an ECD-100 electrochemical detector mfd. by Acome. The voltage was +650 mV (against a SEC electrode).

Results

The drug disposition parameters of each sample were determined from the data obtained by the oral administration of the preparation comprising 3 mg/kg of compound (IX) and 15 mg/kg of L-cysteine or L-aspartic aspartic acid or a control preparation comprising no amino acid to beagles after fasting. The results are given in Table 4.

pH to 5.0. The plasma thus treated was kept frozen at −20° C. The points of collection of blood samples were before the administration and 10, 20, 30 and 45 minutes and 1, 1.5, 2, 3, 4, 6 and 8 hours after the administration.

(b) Method of analysis of concentration of unchanged substance in blood plasma

A similar method to that of Experimental Example 4 was employed.

(c) HPLC determination conditions

A similar method to that of Experimental Example 4 was employed.

Results

The drug disposition parameters of each sample were determined from the data obtained by the oral adminis-

TABLE 4

| Dose of compound (IX) | Added organic acid | n | $T_{max}$ mean ± SE hr | $C_{max}$ mean ± SE ng/ml | AUC (0–8 hr) mean ± SE ng*hr/ml | Addition effect (AUC ratio) |
|---|---|---|---|---|---|---|
| 3 mg/kg | L-Cysteine 15 mg/kg | 2 | 1.17 ± 0.84 | 15.3 ± 2.7 | 24.4 ± 1.0 | 1.59 |
| 3 mg/kg | L-Aspartic acid 15 mg/kg | 2 | 0.75 ± 0.25 | 48.2 ± 2.5 | 37.5 ± 0.2 | 2.46 |
| 3 mg/kg | none (control) | 4 | 0.73 ± 0.28 | 21.0 ± 5.3 | 15.2 ± 2.8 | 1.00 |

Notes)
n: number of beagles,
$T_{max}$: time taken for attaining the maximum plasma concentration,
$C_{max}$: maximum plasma concentration,
AUC: area under the plasma concentration-time curve.

It was found from the results given in Table 4 that the AUC values were increased 1.59-fold and 2.46-fold by adding L-cysteine and L-aspartic acid, respectively. Thus the effects were nearly 2.7 times as much as that obtained by adding tartaric acid, though they were inferior to that obtained by adding ascorbic acid.

EXPERIMENTAL EXAMPLE 5

Samples 350 mg of ascorbic acid and 70 mg of lactose were added to 70 mg of compound (II) and the mixture was thoroughly pulverized and mixed in a mortar. The mixture was filled in each of No. 2 gelatin capsules in such an amount that the dose of compound (II) would be 3 mg/kg to obtain a preparation.

A control sample free from ascorbic acid was prepared by preparing a powder of 7-fold dilution with lactose (70 mg of compound (II) plus 420 mg of lactose) and filled in No. 2 capsules in such an amount that the dose of compound (II) would be 3 mg/kg to obtain a preparation.

Method (a) Administration and collection of blood sample

Four beagles were divided into two groups (i.e. a group to which ascorbic acid was given and a control group) after fasting overnight (14 hours) and a preparation comprising 3 mg/kg of compound (II) and 15 mg/kg of ascorbic acid or a control preparation comprising no ascorbic acid was given together with 30 ml of water by oral administration. No food was given also in the course of collection of blood sample. 3 ml of the whole blood was sampled through a vein of a foreleg by means of a heparinized syringe, immediately cooled with ice/water and centrifuged (1200 rpm, 3 min, 4° C.). The blood plasma was separated and a citrate buffer solution (pH 3.5, 100 μl) was added thereto to adjust the tration of the preparation comprising 3 mg/kg of compound (II) and 15 mg/kg of ascorbic acid or a control preparation comprising no ascorbic acid to beagles while they were kept fasting. The results are given in Table 5.

It is apparent from Table 5 that when the compound (II) having a catechol residue is used, the effect of increasing the AUC value about 1.4-fold is exhibited by adding ascorbic acid, though the effect is not so remarkable.

EXPERIMENTAL EXAMPLE 6

Samples 350 mg of ascorbic acid and 70 mg of lactose were added to 70 mg of compound (III) and the mixture was thoroughly pulverized and mixed in a mortar. The mixture was filled in each of No. 2 gelatin capsules in such an amount that the dose of compound (III) would be 3 mg/kg to obtain a preparation.

A control sample free from ascorbic acid was prepared by preparing a powder of 7-fold dilution with lactose (70 mg of compound (III) plus 420 mg of lactose) and filled in No. 2 capsules in such an amount that the dose of compound (III) would be 3 mg/kg to obtain a preparation.

Method (a) Administration and collection of blood sample

Four beagles were divided into two groups (i.e. a group to which ascorbic acid was given and a control group) after fasting overnight (14 hours) and a preparation comprising 3 mg/kg of compound (III) and 15 mg/kg of ascorbic acid or a control preparation comprising no ascorbic acid was given together with 30 ml of water by oral administration. No food was given also in the course of collection of blood sample. 3 ml of the whole blood was sampled through a vein of a foreleg by means of a heparinized syringe, cooled with ice/water and centrifuged (1200 rpm, 3 min, 4° C.). The blood plasma was separated and a citrate buffer solution (pH 3.5, 100 μl) was added thereto to adjust the pH to 5.0. The plasma thus treated was kept frozen at −20° C. The points of collection of blood samples were before the administration and 10, 20, 30 and 45 minutes and 1, 1.5, 2, 3, 4, 6 and 8 hours after the administration.

(b) Method of analysis of concentration of unchanged substance in blood plasma

A similar method to that of Experimental Example 4 was employed.

(c) HPLC determination conditions

A similar method to that of Experimental Example 4 was employed.

Results

The drug disposition parameters of each sample were determined from the data obtained by the oral administration of the preparation comprising 3 mg/kg of compound (III) and 15 mg/kg of ascorbic acid or a control preparation comprising no ascorbic acid to beagles while they were kept fasting. The results are given in Table 5.

It is apparent from Table 5 that when the compound (III) having a catechol residue is used, the effect of increasing the AUC value about 3.3-fold is exhibited by adding ascorbic acid.

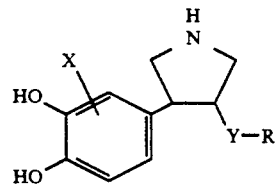

(I)

wherein X represents a hydrogen atom, a halogen atom or a lower alkyl group, Y represents a group of the formula: $(CH_2)_n$— in which n is zero or an integer of 1 to 2, a group of the formula:

in which p is zero or an integer of 1 to 2, a group of the formula: —O— or a group of the formula: —NH—, and R represents a substituted or unsubstituted phenyl group, a substituted or unsubstituted naphthyl group or a heteroaryl group.

5. The preparation according to claim 4, wherein the substituted or unsubstituted phenyl group is represented by the formula:

TABLE 5

| Catechol compound | Added organic acid | n | $T_{max}$ mean ± SE hr | $C_{max}$ mean ± SE ng/ml | AUC (0–8 hr) mean ± SE ng*hr/ml | Addition effect (AUC ratio) |
|---|---|---|---|---|---|---|
| compound (II) 3 mg/kg | Ascorbic acid 15 mg/kg | 2 | 0.63 ± 0.13 | 89.6 ± 11.8 | 116.6 ± 0.1 | 1.39 |
| compound (II) 3 mg/kg | none (control) | 2 | 0.42 ± 0.09 | 95.6 ± 42.2 | 83.6 ± 4.7 | 1.00 |
| compound (III) 3 mg/kg | Ascorbic acid 15 mg/kg | 2 | 0.50 ± 0.25 | 91.9 ± 0.4 | 197.1 ± 12.5 | 3.29 |
| Compound (III) 3 mg/kg | none (control) | 2 | 0.75 ± 0.25 | 39.0 ± 16.6 | 59.8 ± 16.9 | 1.00 |

Notes)
n: number of beagles,
$T_{max}$: time taken for attaining the maximum plasma concentration,
$C_{max}$: maximum plasma concentration,
AUC: area under the plasma concentration-time curve.

We claim:

1. A solid oral preparation comprising an organic acid, or a salt thereof selected from the group consisting of ascorbic acid, citric acid, tartaric acid, aspartic acid and cysteine, and a pyrrolidine derivative having a catechol group, or a pharmacologically acceptable salt thereof.

2. The preparation according to claim 1, wherein the organic acid is ascorbic acid, citric acid or tartaric acid.

3. The preparation according to claim 1, wherein the organic acid is aspartic acid or cysteine.

4. The preparation according to claim 1, wherein the pyrrolidine derivative having a catechol group is represented by the following general formula (I), or a pharmacologically acceptable salt thereof:

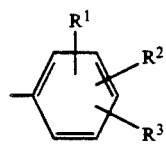

wherein $R^1$, $R^2$ and $R^3$ may be the same or different from one another and each represent a hydrogen atom, a lower alkyl group, a lower alkoxy group, a halogen atom, a hydroxyl group, a trifluoromethyl group or a group of the formula:

in which $R^4$ and $R^5$ may be the same or different and each is a hydrogen atom or a lower alkyl group.

6. The preparation according to claim 1, wherein the pyrrolidine derivative is trans-3-(2-chloro-3-hydroxyphenyl)-4-(3,4-dihydroxyphenyl)pyrrolidine.

7. The preparation according to claim 1, wherein the pyrrolidine derivative is a compound of the following formula (II), or a pharmacologically acceptable salt thereof:

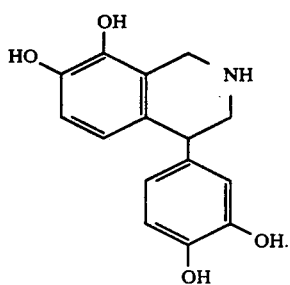 (II)

8. The preparation according to claim 1, wherein the pyrrolidine derivative is a compound of the following formula (III), or a pharmacologically acceptable salt thereof:

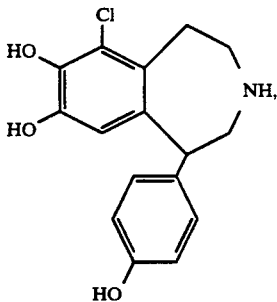 (III)

9. The preparation according to claim 1, wherein the amount of the organic acid, or salt thereof, is 5 to 80% by weight, based on the total solid oral preparation.

10. The preparation according to claim 1, wherein the pyrrolidine derivative is trans-3-(2-chloro-3-hydroxyphenyl)-4-(3,4-dihydroxyphenyl)pyrrolidine hydrochloride.

11. The preparation according to claim 10, wherein the organic acid is ascorbic acid.

12. The preparation according to claim 10, wherein the organic acid is tartaric acid.

13. The preparation according to claim 10, wherein the organic acid is citric acid.

14. The preparation according to claim 7, wherein the organic acid is ascorbic acid.

15. The preparation according to claim 8, wherein the organic acid is ascorbic acid.

16. The preparation according to claim 1, wherein the organic acid is L-cysteine.

17. The preparation according to claim 1, wherein the pyrrolidine derivative is trans-3-(2-chloro-3-hydroxyphenyl)-4-(3,4-dihydroxyphenyl)pyrrolidine hydrobromide.

* * * * *